United States Patent

Horn et al.

Patent Number: 5,591,230
Date of Patent: Jan. 7, 1997

[54] RADIALLY EXPANDABLE STENT

[75] Inventors: Joseph B. Horn, Niwot, Colo.; Ivan De Scheerder, St. Martens Latem, Belgium

[73] Assignee: Global Therapeutics, Inc., Broomfield, Colo.

[21] Appl. No.: 514,069

[22] Filed: Aug. 11, 1995

Related U.S. Application Data

[63] Continuation-in-part of Ser. No. 456,087, May 31, 1995.

[30] Foreign Application Priority Data

Sep. 7, 1994 [BE] Belgium .............................. 09400801

[51] Int. Cl.$^6$ ...................................................... A61F 2/06
[52] U.S. Cl. .................. 623/1; 623/11; 623/12; 606/194; 606/195
[58] Field of Search .................. 623/1, 11, 12; 606/194, 195

[56] References Cited

U.S. PATENT DOCUMENTS

| | | | |
|---|---|---|---|
| 4,733,665 | 3/1988 | Palmaz | 128/343 |
| 4,856,516 | 8/1989 | Hillstead | 128/343 |
| 4,886,062 | 12/1989 | Wiktor | 128/343 |
| 4,907,336 | 3/1990 | Gianturco | 29/515 |
| 5,041,126 | 8/1991 | Gianturco | 606/195 |
| 5,104,404 | 4/1992 | Wolff | 623/1 |
| 5,135,536 | 8/1992 | Hillstead | 623/1 |
| 5,147,385 | 9/1992 | Beck et al. | 623/1 |
| 5,161,547 | 11/1992 | Tower | 128/898 |
| 5,183,085 | 2/1993 | Timmermans | 623/1 |
| 5,217,483 | 6/1993 | Tower | 606/198 |
| 5,292,331 | 3/1994 | Boneau | 606/198 |
| 5,304,200 | 4/1994 | Spaulding | 623/1 |
| 5,314,444 | 5/1994 | Gianturco | 606/195 |
| 5,389,106 | 2/1995 | Tower | 623/1 |
| 5,443,498 | 8/1995 | Fontaine | 623/1 |

*Primary Examiner*—John G. Weiss
*Assistant Examiner*—Francis K. Cuddihy
*Attorney, Agent, or Firm*—Sheridan Ross P.C.

[57] ABSTRACT

The present invention is directed to a radial expandable stent for use in blood vessels. The length of the stent after expansion is substantially the same as the stent length before expansion. The stent is annealed at high temperatures to permit the wire to form an original multi-loop design including a plurality of concentric bended loops in a continuous wire folded along a length thereof. This provides desired alignment of the stent in the blood vessel in order to enhance desired blood flow and thereby reduce thrombogenicity.

28 Claims, 6 Drawing Sheets

RADIALLY EXPANDABLE STENT

The present application is a continuation-in-part application of U.S. patent application entitled "Radially Expandable Stent" having Ser. No. 08/456,087 pending filed May 31, 1995, incorporated herein by this reference in its entirety and claims priority from a Belgium patent application entitled "A New Intravascular Prosthesis (IDS-STS-2) For the Treatment of Dissected and Stenosed Blood Vessels", having Ser. No. 09400801 filed Sep. 7, 1994, incorporated herein by this reference in its entirety.

FIELD OF THE INVENTION

The present invention is generally directed to a stent for use in blood vessels and specifically to a radially expandable stent for treating blood vessel constrictions.

BACKGROUND OF THE INVENTION

Balloon catheters and stents are normally used for treating blood vessel constrictions. Although balloon catheters are effective in dilating constrictions, they can not only result in a dissection in the blood vessel (which causes the vessel to close and acute myocardial infarction to occur) but also increase the risk of restenosis, e.g., another constriction occurring in the same portion of the blood vessel at a later time. Stents are commonly employed to overcome these problems. Stents are hollow tubes that are implanted inside of the blood vessel to "prop" the vessel open and prevent blood vessel constrictions and blockages.

Stents are available in a variety of configurations including self-expanding springs, mechanically actuated expandable devices, heat actuated expandable devices, and balloon expandable devices. Radial expanded stents are mounted on a collapsed balloon catheter and, after introduction into the vessel, are expanded by balloon pressure. The deployed stent contacts and supports the interior wall of the blood vessel.

Though widely used, stents can have a number of limitations and can cause health complications. For example, stents can be limited in the radial strength of the stent (thereby limiting the amount of support provided to the interior wall of the blood vessel), in the maximum size of the stent (e.g., maximum stent diameter) after expansion (thereby limiting the stent to use in smaller diameter vessels), and/or in the minimum size of the stent profile that is to be inserted into the vessel (thereby limiting the stent to use in larger diameter vessels). Stents can also cause health complications after implantation including thrombogenic occlusion of the blood vessel (e.g., blood clots), restenosis (e.g., re-narrowing of the lumen of the blood vessel), distal dissection, and injury to the interior wall of the blood vessel wall during stent insertion, which can cause bleeding.

There is a further need for a stent having a broad range of sizes (e.g., diameters and lengths) after expansion for use in blood vessels of a variety of sizes to permit customized stenting.

There is a further need for a stent having a low risk of injury to the blood vessel during insertion.

There is a further need for a stent that has a low risk of thrombosis after implantation in a blood vessel.

There is a further need for a stent that has a relatively low incidence of neointimal hyperplasia after implantation.

SUMMARY OF THE INVENTION

The present invention addresses these and other needs by providing a stent for use in a blood vessel that includes a plurality of concentric bended loops in a continuous wire folded along a length thereof. In a first state, the concentric bended loops have a first mean diameter. In a second state after placement in the vessel by inflation of a balloon catheter, the concentric loops have a second mean diameter, that is larger than the first mean diameter by enlarging the angle of the bends of the concentric loops. The substantially cylindrical member deforms plastically, for example, expansion by a balloon.

The substantially cylindrical member includes proximal and distal ends and a number of interconnected, substantially circular, concentric loops disposed between the two ends. Each loop has a bend in each quadrant of a substantially circular cross-section of the substantially cylindrical member to permit the substantially cylindrical member to expand in the second state and conform to the walls of the vessel while maintaining the length of the substantially cylindrical member substantially constant. The bends are separated from one another by a leg member.

The bends in the loops form angles between the leg members that have differing magnitudes in the first and second states. In the first state, the angles range from about 10 to about 50 degrees and in the second state the angles range from about 30 to about 120 degrees. As will be appreciated, the angles in the first state are no more than, and preferably less than, the angles in the second state. For tortuous vessels, the bends can have angles that vary in magnitude along the length of the substantially cylindrical member.

The substantially cylindrical member preferably has a distribution of loops along its length ranging from about 3 to about 10 loops/cm. The length of the member typically ranges from about 8 mm to about 50 cm.

For best results, the stent in the second state has an outer diameter that is greater than the inner diameter of the vessel. This inhibits recoil of the stent in the vessel in response to the elasticity of the blood vessel. Preferably, the outer diameter of the stent is at least about 0.25 mm to larger than the vessel inner diameter.

In one embodiment, the stent includes a substantially cylindrical member formed from a continuous length of wire, with the member including a number of interconnected, substantially circular, concentric loops disposed between proximal and distal ends. The loops have a bend that form an angle. Along a length of the member, a line bisecting the angles in a number of the loops is substantially parallel to the direction of blood flow through the vessel after implantation of the stent. The alignment of the bends reduces the impedance of the stent to the blood flow relative to existing stents.

The line can be in the same plane that includes the central axis of the member. In this original configuration, the axis of the member is substantially parallel to the direction of blood flow in the vessel.

The loops can have a number of bends with adjacent bends being separated by a leg member. Preferably, each quadrant of the loop has no more than one bend. At least two of the leg members in a loop are preferably of different lengths to permit alignment of the bends along the length of the member.

The present invention further includes a method for deploying the stent in a vessel in a body. The method includes the steps: (i) selecting a length for the stent that is sufficient to treat the length of the diseased portion of the vessel wherein the stent is longer than the selected length; (ii) cutting the stent to the selected length; and (iii) deploying the stent in the blood vessel after the cutting step.

The selecting step preferably selects a length of the stent such that the stent length is preferably at least about 4 mm longer than the length of the diseased portion of the vessel. Thus, the invention can provide a stent that has a length sufficient for treating any length of diseased vessel.

The present invention includes a method for manufacturing the stent. The method includes the steps: (i) first annealing a wire, preferably a 316 LVM stainless steel wire, at a temperature ranging from about 800° to about 1200° C.; (ii) forming the wire into the stent manually or automatically using a machine; and (iii) second annealing the stent at a temperature ranging from about 800° to about 1200° C. In step (i) and/or (ii), the temperature more preferably ranges from about 950° to about 1100° C. and most preferably from about 950° to about 1050° C.

The present invention has a number of advantages relative to prior art stent devices. By way of example, the stent after expansion is better aligned to the vessel reducing blood turbulence resulting in less thrombogenicity of the stent. Further, after expansion, the length of the stent is substantially the same length as the stent before expansion. This feature permits doctors to select a stent which will extend the entire length of the diseased portion of the blood vessel after implantation. In contrast, existing stent devices have a length after implantation that is significantly less than the stent length before expansion. As a result, the stent length after expansion can be insufficient to extend the entire length of the diseased portion of the blood vessel and to stabilize the dissected portion of the vessel which can cause restenosis and/or thrombosis. The stent also is substantially stable in the blood vessel after implantation. The stability of the stent in the blood vessel thereby reduces the risk of embolization. Other advantages are set forth in the detailed discussion of the invention below.

DETAILED DESCRIPTION

Figure 1:
FIGS. 1–3 depict front, plan and side views of an embodiment of the present invention before expansion.

Referring to FIGS. 1–4, a stent 20 according to the present invention is depicted before expansion (e.g., in a first state). The stent 20 has a substantially cylindrical profile and includes a distal end 24, a proximal end 28, and a plurality of concentric, interconnected support assemblies 32a,b, or loops, between the distal and proximal ends 24, 28. Each of the support assemblies 32 includes at least one, and preferably two, apex members 36a,b and connector members 40a,b, and at least four leg members 44a,b. The stent 20 is especially useful for treating blood vessel constrictions in humans and animals and complications arising during diagnostic procedures for cardiac and vascular conditions.

The stent 20 is formed from a substantially continuous length of wire 50 and is free of connecting joints or welds between the distal and proximal ends 24,28. The absence of joints and welds in this portion of the stent 20 provides increased radial strength for the stent 20 relative to existing stent devices. The increased strength provides a significantly reduced incidence of stent failure during use.

The stent 20 has a length preferably ranging from about 8 mm to about 40 cm, and more preferably ranging from about 8 mm to about 10 cm, with the distribution of support assemblies 32 along the stent length ranging from about 3 to about 50 support assemblies/cm, and more preferably ranging from about 3.5 to about 6.5 support assemblies/cm, to yield a distance between adjacent support assemblies preferably ranging from about 0.2 to about 3.0 mm, and more preferably from about 0.3 to about 1.0 mm. As will be appreciated, if the distance between adjacent support assemblies 32a,b is too great, intimal flaps on the interior wall of the blood vessel can be trapped between the support assemblies and protrude into the blood vessel, thereby decreasing the luminal (e.g., cross-sectional area) area of the vessel.

Adjacent support assemblies 32a,b preferably do not contact one another except at the leg members 44. Adjacent support assemblies 32 share the same leg member 44 at the junction between the support assemblies. By way of example, support assembly 32a and support assembly 32b share one of the leg members 44a, and support assembly 32b and support assembly 32c share one of the leg members 44b and so on to form the stent 20. The apex and connector members are independent of and preferably do not contact an adjacent support assembly 32.

The apex and connector members 36,40 are formed between adjacent leg members 44 and are slightly rounded with no sharp edges to avoid injury to the interior wall of the blood vessel or puncture of the balloon catheter during balloon dilation. The apex and connector members are formed by bending the wire to form an angle 46. The angle 46 preferably ranges from about 10 to about 50 degrees and more preferably from about 40 to about 50 degrees. The angles 46 in the various apex and connector members 36,40 of all of the support assemblies 32 along the length of the stent are preferably substantially the same magnitude. The apex members 36 are preferably positioned downstream of the connector members 40.

Figure 2:
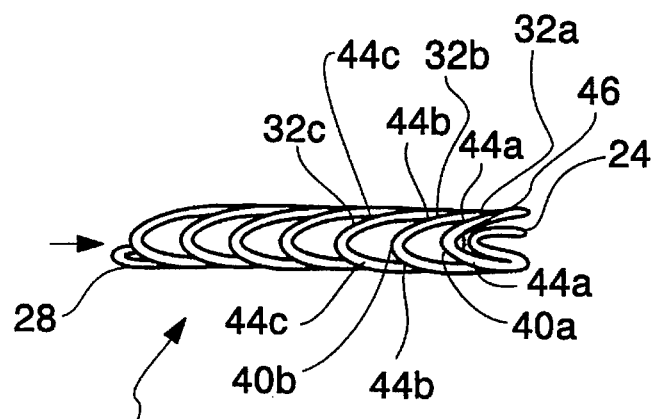
Figure 3:
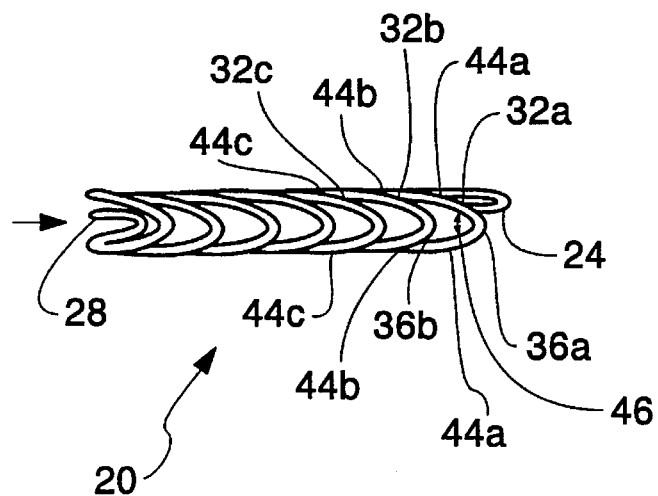
Figure 4:
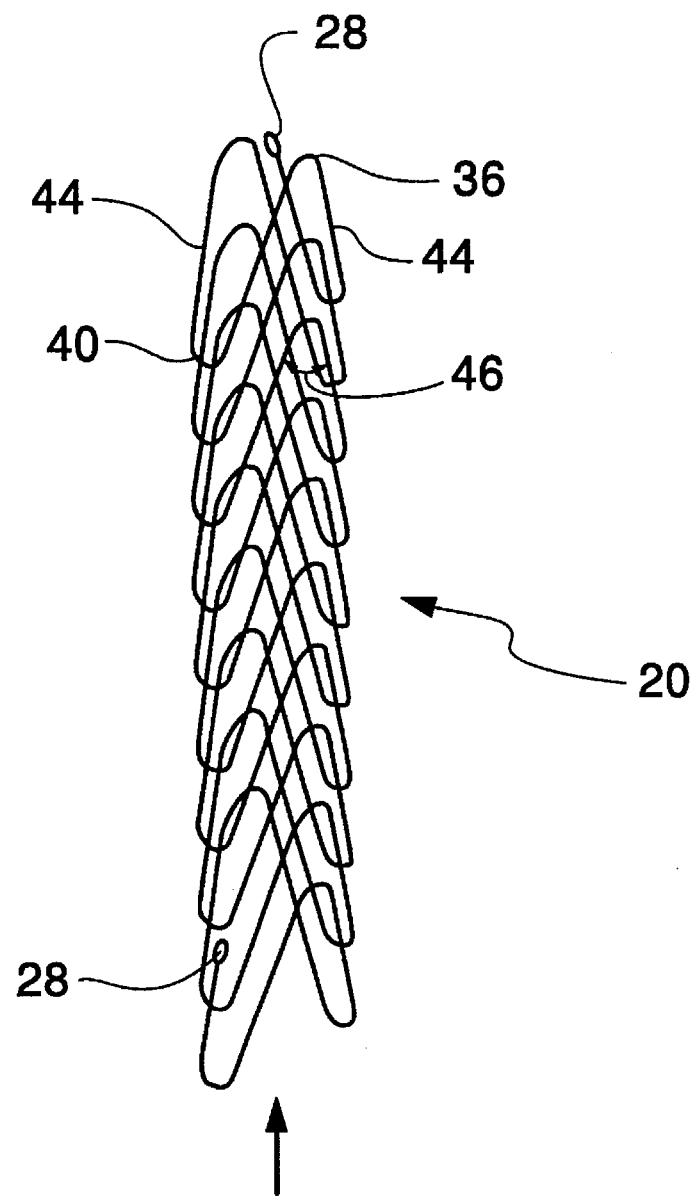
FIG. 4 is a perspective view of the embodiment.

As can be seen from FIGS. 2 and 3, an important feature of the present invention is the alignment of the apex members and connector members along the length of the stent 20. A line 45 bisects the angles 46 at the various apex members and connector members with the line 45 being substantially parallel to the flow of blood through the stent 20. It is preferred that the lines 45a,b of the apex members and connector members, respectively, be coplanar with the longitudinal axis of the stent 20. The alignment of the apex and connector members relative to the direction of blood flow provide reduced impedance to blood flow relative to existing stents. It is believed that the alignment inhibits the turbulence in the blood stream as it passes through the stent. The reduced turbulence reduces the likelihood of blood clot formation relative to the existing stents.

The leg members 44 in the support assemblies are preferably of two different lengths. It has been determined that the different lengths are required for alignment of the apex and connector members. Adjacent leg members are thus of different lengths with alternating leg members being of the same length. Preferably, the length of the leg members 44 ranges from about 2 mm to about 15 mm.

The distal and proximal ends 24,28 are shaped to avoid injury to the blood vessel wall and/or puncture of the balloon catheter during insertion. Accordingly, the distal and proximal ends are generally bent inward or welded to provide a rounded profile. The proximal end 28 is preferably located upstream of the distal end 24.

The composition of the wire 50 in the stent 20 can be selected from a variety of suitable metals, such as stainless steel, nitinol, tantalum, and platinum. For best results, stainless steel is employed. Stainless steel has a high radial strength and is relatively nonthrombogenic, especially stainless steel that has a low carbon content and was formed by vacuum molding techniques. The preferred stainless steel is a 316 LVM stainless steel wire. In some cases, however, it is desirable to remove the stent after a period of time to reduce the likelihood of thrombosis. In such cases, materials such as nitinol and tantalum are preferred.

The diameter of the wire 50 in the stent 20 preferably ranges from about 0.13 to about 0.24 mm. The wire diameter within this range selected for a specific application is based on the diameter of the blood vessel. For example, for blood vessel diameters ranging from about 2.5 to about 3.5 mm the wire diameter is preferably about 0.18 mm, from about 3.5 to about 6.0 mm the wire diameter is preferably about 0.20 mm, and from about 6.0 to about 10.0 mm the wire diameter is preferably about 0.24 mm.

Figure 5:
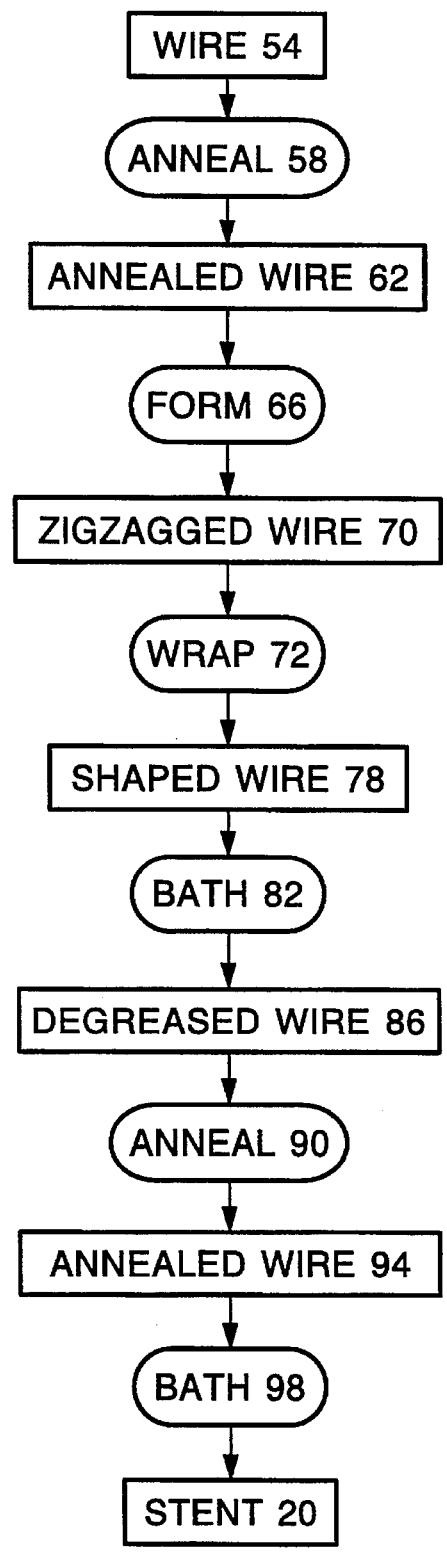
FIG. 5 is a flow schematic of the process to manufacture the embodiment of the present invention.

Referring to FIG. 5, the process for manufacturing the stent 20 will now be described. The process is an important aspect of the alignment and shape adaptability of the stent relative to the vessel as compared to existing devices.

In the first step, the wire 54 is annealed 58 under a vacuum atmosphere at a temperature preferably ranging from about 800° to about 1200° C., more preferably from about 950° to about 1100° C., and most preferably from about 950° to about 1050° C. for a time preferably ranging from about 0.5 to about 2.0 hours and more preferably from about 0.75 to about 1.5 hours. The vacuum removes gases, such as oxygen, that can oxidize the wire surface. As will be appreciated, the annealing step can also be conducted in an inert atmosphere that is substantially free of gases such as oxygen.

Figure 6:
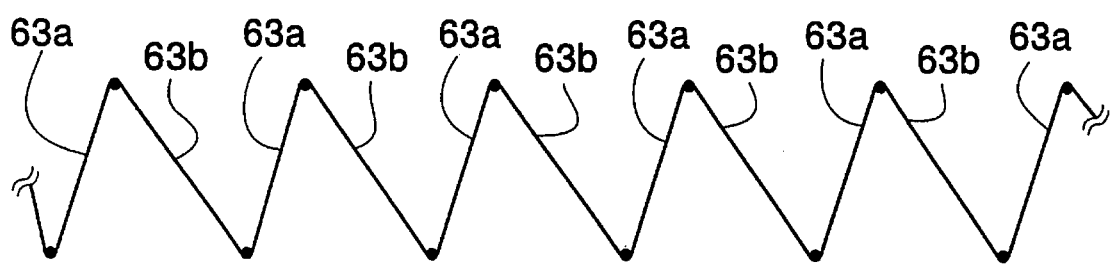
FIGS. 6–7 depict steps in manufacturing of the embodiment.

Referring to FIGS. 5–6, the annealed wire 62 is formed 66 on a die, which may be done manually or automatically using a machine, to the desired zigzag shape to form a zigzagged wire 70. The adjacent leg members 63a,b in the zigzagged wire are of different lengths with the two sets of alternating leg members 63a and 63b being of the same lengths. The die can be a plurality of pins staggered such that a wire wrapped around the pins produces the zigzag shape in the wire. The high temperatures in the annealing step substantially eliminate the shape memory of the wire and thereby make it adapt readily to the zigzag shape. Preferably, there are from about 3.0 to about 6.0 cycles/cm in the zigzagged wire 70.

Figure 7:
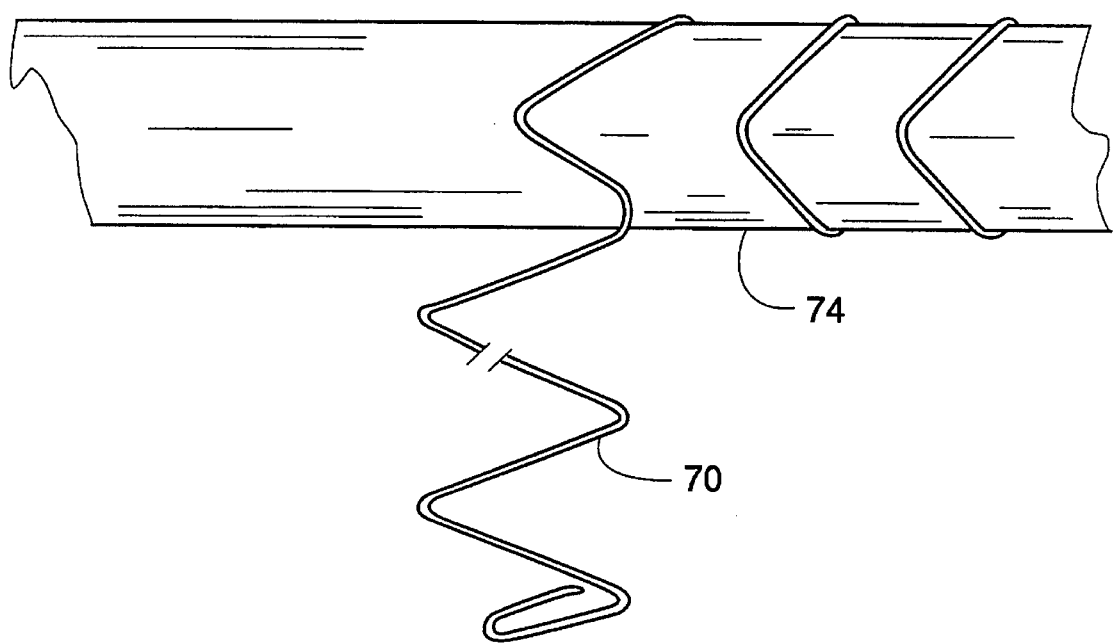

Referring to FIGS. 5 and 7, the zigzagged wire 70 is wrapped 72 around a dowell 74 in a spiral or helical fashion to form a shaped wire 78. As the wire is wrapped around the dowell, adjacent sets of the apex and connector members are aligned as noted above. The dowell 74 is preferably a 5–20 French tubular device and is more preferably a 6–12 French device and most preferably a 6 French device.

The shaped wire 78 is immersed in an ultrasonic bath 82 for approximately 30 minutes to yield a degreased wire 86. The bath contains a degreasing solution to remove grease, oils and other residues and particulates on the shaped wire 78.

The degreased wire 86 is then annealed 90 a second time under vacuum at the temperatures and times noted above to eliminate the shape memory of the wire and thereby make it adapt readily to the expanded shape in the blood vessel.

The annealed wire 94 is again immersed in an ultrasonic bath 98 to remove residue from the wire. The bath contains distilled water and is substantially free of degreasing solution. Distilled water permits the removal of materials from the wire that can cause complications after implantation in a patient.

After the above-described process, the stent of the present invention is relatively soft and flexible compared to many existing stent devices. The relative softness of the stent makes it deform plastically under low pressures to the desired shape aligned to the vessel. The flexibility of the stent enables it to be inserted in blood vessels having sharp bends and/or tortuous paths.

Figure 8:
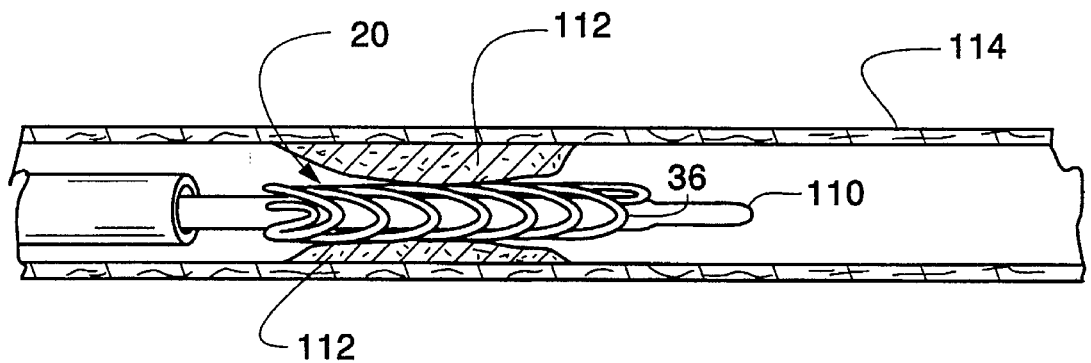
FIGS. 8–9 are various views depicting the implantation of the embodiment in a blood vessel.
Figure 9:
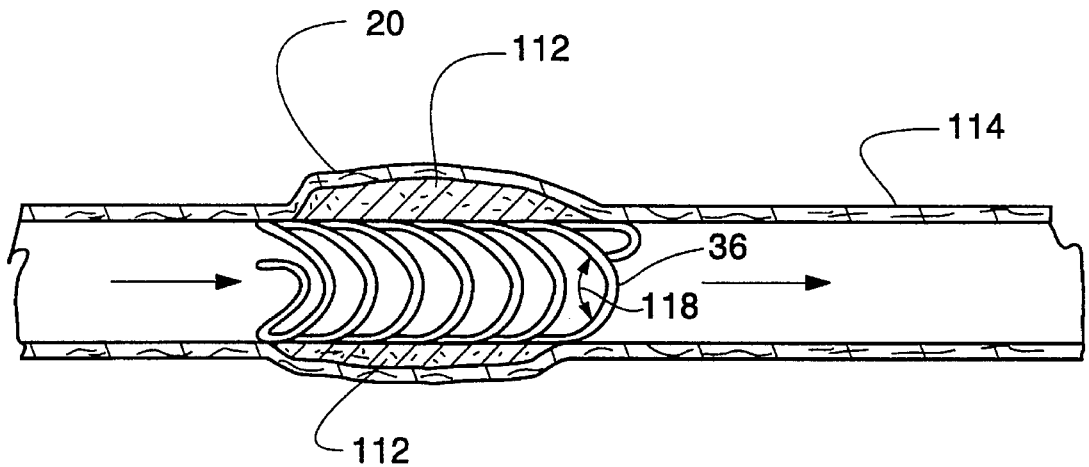

Referring to FIGS. 8–9, the implantation and operation of the stent will be described. The first step in implanting the stent is to select the proper post expansion stent diameter and length. The stent preferably has an outer post expansion diameter ranging from about 2.5 to about 10.0 mm and more preferably from about 3.0 to about 5.0 mm in size. The length of the stent is preferably sufficient to extend not only the length of the diseased portion of the blood vessel but also no less than about 2 mm on either side of the diseased portion. Thus, the preferred stent length is the length of the diseased portion plus an additional 4 mm to overlap the adjacent healthy portions of the vessel.

In one embodiment, the stent is cut to the desired length. This permits one stent length to be used for all possible desired lengths. This avoids the need for a multiplicity of stents to treat relatively long diseased areas. As will be appreciated, the use of a multiplicity of overlapping stents to treat such relatively long areas is common for existing stents. Such a practice is more expensive than using a single stent and has an increased risk of subacute thrombosis and an increased risk of restenosis at the points at which adjacent stents overlap.

In this embodiment, a desired length is first selected for the stent that is sufficient to treat the diseased portion of the vessel. The stent is then cut to the desired length. Existing stents are not available in this flexibility of lengths as existing stents generally are sold in a limited range of sizes. As noted above, this limited selection in stent lengths requires a multiplicity of overlapping stents to be used to treat relatively long diseased areas of blood vessels.

As shown in FIG. 8, the stent 20 is placed over the deflated balloon catheter 110 and compressed to embed the stent 20 into the balloon 110 before insertion into the blood vessel 114. The substantially cylindrical profile of the stent 20 on the balloon catheter 110 is relatively small and permits the use of a smaller guide catheter (e.g., a 6 french guide catheter of at least about 0.62 inch inner diameter as opposed to 0.78 inch used in existing stent devices) and provides the ability to pass sharp bends or corners and negotiate tortuous paths in the blood vessel 114.

After insertion of the balloon catheter 110 and stent 20 into the blood vessel 114, the balloon and stent are moved to the desired location in the blood vessel to compress plaque 112 and open up the blood vessel 114. The position of the balloon and stent in the vessel are determined by fluoroscopic or other suitable means.

When the balloon 110 and stent 20 are in the desired position, the balloon 110 is inflated to a pressure that will fully expand the balloon. The pressure to plastically deform the stent is preferably less than about 15 atms, preferably ranging from about 5 to about 14 atms, more preferably ranging from about 6 to about 10 atms, and most preferably from about 7 to about 8 atms. As the balloon 110 fully expands, the stent plastically deforms into a second state. The stent diameter is larger than the stent diameter in the first state with the lengths of the original (e.g., unexpanded) and expanded stent being substantially the same. The stent length after expansion preferably is at least about 95%, more preferably at least about 98%, and most preferably at least about 99% of the original (unexpanded) stent length.

The substantial maintenance of the original stent length after expansion results from the unique manner in which the stent changes shape. The angle 46 in each apex and connector member increases in magnitude to form second angles 118 and thereby provides the increased stent diameter without a shortening of the stent. The second angles 118 in the apex and connector members preferably range from about 30 to about 120 degrees and more preferably from about 40 to about 100 degrees.

The stent diameter after expansion is determined by the diameter of the balloon catheter used for deploying the stent. It is desirable to use a balloon catheter having a diameter sufficient to provide an outer stent diameter that is about 0.25 to about 0.50 larger than the interior diameter of the blood vessel. The outer diameter of the stent at full expansion preferably ranges from about 2.5 to about 50.0 mm and more preferably ranges from about 3.0 to about 10.0 mm and most preferably about 3.0 to about 6.0 for coronary arteries.

The stent of the present invention can expand to a much greater degree than existing stent devices. Accordingly, a single size of stent is able to be expanded to treat a broad range of blood vessel sizes. This feature provides ease of use by physicians at a reduced cost (due to a reduced stent inventory). By way of example, a single stent can produce a blood vessel diameter ranging from about 2.5 to about 50 mm. Stents 20 can be used for blood vessels having diameters preferably ranging from about 2.5 to about 10.0 mm and more preferably from about 3.0 mm to about 5.0 mm for coronary vessels.

After the constriction formed by the plaque 112 is compressed and the stent properly expanded, the balloon catheter 110 is deflated and removed from the stent 20 and blood vessel 114.

Referring to FIG. 9, the expanded stent after removal of the balloon catheter 110 maintains its shape 114 and experiences no movement in the blood vessel 114. The stability of the stent of the present invention is due to the softness and flexibility of the metal wire in the stent coupled with the stent design. The stent softness and flexibility and zigzag configuration permit the stent to plastically deform to substantially match the shape of the blood vessel resulting in less blood turbulence, shear stress, blood impedance with lower thrombogenicity in the vessel. As will be appreciated, blood vessels normally have a diameter and shape that fluctuate along a given length of the blood vessel. Accordingly, along the length of the stent the angles 118 in each support assembly 32 can have differing magnitudes depending upon the diameter and shape of the blood vessel.

To further reduce the thrombogenicity of the stent, the stent can have a coating of an anti-coagulant. However, the stent has an acceptable degree of thrombogenicity without the use of such a coating. In most applications, the stent has an acceptable degree of thrombogenicity due to the original stent design and the high degree of biocompatability of the 316 LVM stainless steel wire without the use of such a coating.

EXAMPLE

The stent was used in experimental trials to determine its effectiveness in actual use. It was discovered that the stent could be placed very far distally and navigate sharp bends in the blood vessel.

The stent was also found to be reliable. No problems were encountered with the proper placement of the stent and balloon rupture. The placement of the stent did not give rise to problems associated with the withdrawal of the balloon. These problems occur with existing devices used under the same experimental conditions.

Angiographic controls after placement of the stents showed a well opened vascular lumen without intravascular haziness and signs of distal or proximal dissection. It also appeared that the side branches at the level of the vessel segment bearing the stent were intact.

Follow-up investigations after 7 days showed that the entire stent remained open without thrombotic developments, though no anticoagulant therapy was administered in the study.

Follow-up investigations after 6 weeks showed that no substantial reactive neointimal growth was induced by the stent.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the appended claims.

What is claimed is:

1. An expandable stent for implantation within a blood vessel in a body, comprising:

a substantially cylindrical member formed from a continuous length of wire, wherein said substantially cylindrical member includes a plurality of interconnected, substantially circular, concentric loops disposed between a proximal and distal end thereof, wherein, when said substantially cylindrical member is implanted in the blood vessel, a plurality of said concentric loops, each having an angular-shaped bend with no more than one angular shaped bend being located in each quadrant of each of said loops, said bend in each of said plurality of concentric loops forming an angle, and, along a length of said substantially cylindrical member, a line bisects a plurality of said angles, and wherein, when said substantially cylindrical member is in place in the blood vessel, said line is maintained substantially parallel to a direction of blood flow through the blood vessel to reduce an impedance of said substantially cylindrical member to the blood flow.

2. The stent according to claim 1, wherein a same size of said substantially cylindrical member is used in blood vessels having diameters in a range of about 2.5–5.0 mm.

3. The stent according to claim 1, wherein an average distance between adjacent concentric loops along the length of said substantially cylindrical member ranges from about 0.3 to about 1.0 mm.

4. The stent according to claim 1, wherein a substantially cylindrical, circular, concentric loop has a plurality of bends with adjacent bends being separated by a leg member and wherein at least two of said leg members have different lengths.

5. The stent according to claim 1, wherein said substantially cylindrical member is free of welds between said proximal and distal ends for substantially any length of stent.

6. The stent according to claim 1, wherein a plurality of said loops have a bend in each quadrant of a substantially circular cross-section of said substantially cylindrical member to permit said substantially cylindrical member to expand and conform to a size and shape of the vessel while maintaining the length of the substantially cylindrical member substantially constant.

7. The stent according to claim 1, wherein in a first state before implantation of the substantially cylindrical member in the blood vessel said angles range from about 10 to about 50 degrees.

8. The stent according to claim 1, wherein in a first state before implantation of the substantially cylindrical member in the blood vessel the second plurality of said concentric loops each have a bend and wherein in a second state when the substantially cylindrical member is implanted in the blood vessel an average magnitude of said angles in said second state is greater than an average magnitude of the angles in said first state.

9. The stent according to claim 8, wherein in said second state the average magnitude of said angles range from about 30 to about 120 degrees.

10. The stent according to claim 8, wherein said angles each have a magnitude and the magnitudes of said angles in said second state depend upon a shape and size of the vessel.

11. The stent according to claim 1, wherein said angles each have a magnitude and the magnitudes of said angles in said second state vary along the length of said substantially cylindrical member to conform to the shape of said blood vessel.

12. The stent according to claim 1, wherein each loop includes at least four leg members, with a leg member being located between each of said bends.

13. The stent according to claim 12, wherein each of said leg members has a length ranging from about 2 to about 15 mm.

14. The stent according to claim 1, wherein a distribution of said loops between said proximal and distal ends ranging from about 3 to about 50 loops/cm.

15. The stent according to claim 1, wherein said substantially cylindrical member has a length and the length of said substantially cylindrical member ranges from about 8 mm to about 40 cm.

16. The stent according to claim 1, wherein said substantially cylindrical member is substantially free of shape memory.

17. The stent according to claim 1, wherein when the substantially cylindrical member is implanted in the blood vessel an outer diameter of said substantially cylindrical member is at least about 0.25 to about 0.50 mm larger than a vessel interior diameter where said substantially cylindrical member is contacting the vessel.

18. An expandable stent for implantation within a blood vessel, comprising:

a substantially cylindrical member formed from a continuous length of wire, wherein said substantially cylindrical member includes a plurality of interconnected, substantially circular, concentric loops disposed between a proximal and a distal end thereof, with the centers of a plurality of said concentric loops being located along a longitudinal axis of said substantially cylindrical member, wherein each of two adjacent first and second concentric loops have at least four bends with a bend being in each quadrant of each of said first and second concentric loops, wherein said first concentric loop is nearer said proximal end than said second concentric loop and at least two of said bends in said first concentric loop are in opposite quadrants of said first concentric loop and at least two of said bends in said second concentric loop are in opposite quadrants of said second concentric loop and wherein a first distance from said at least two of said bends in said second concentric loop to said proximal end of said substantially cylindrical member is greater than a second distance from said at least two of said bends in said first concentric loop to said proximal end of said substantially cylindrical member, whereby the lodging of an intimal flap on an interior wall of said blood vessel between said first and second concentric loops is inhibited.

19. The stent according to claim 18, wherein, when said substantially cylindrical member is implanted in the blood vessel, a plurality of said concentric loops each have a bend, said bend in each concentric loop forming an angle, such that, along a length of said substantially cylindrical member, a line bisecting said angles in a plurality of said bends is substantially parallel to a direction of blood flow through the blood vessel to reduce an impedance of said substantially cylindrical member to blood flow.

20. The stent according to claim 19, wherein the blood vessel has an interior and the interior of the blood vessel has an irregular shape and, when said substantially cylindrical member is implanted in the blood vessel, the magnitudes of a number of said angles vary along a length of said substantially cylindrical member to conform to the shape of said blood vessel.

21. The stent according to claim 18, wherein said substantially cylindrical member is substantially free of shape memory.

22. The stent according to claim 18, wherein a distribution of said loops ranges from about 3 to about 5.0 loops/cm.

23. The stent according to claim 18, wherein said substantially cylindrical member has a length and an average distance between adjacent loops along the length of said substantially cylindrical member ranges from about 0.2 to about 3.0 mm.

24. The stent according to claim 18, wherein said substantially cylindrical member has a length and an average distance between adjacent loops along the length of said substantially cylindrical member ranges from about 0.3 to about 1.0 mm.

25. The stent according to claim 18, wherein said at least two of said bends in said first concentric loop are each in a different quadrant of a substantially cylindrical cross-section of said substantially cylindrical member than said at least two of said bends in said second concentric loop.

26. An expandable stent for implantation within a blood vessel, comprising:

a substantially cylindrical member formed from a continuous length of wire, wherein said substantially cylindrical member includes a plurality of interconnected, substantially circular, concentric loops disposed between a proximal and a distal end thereof, wherein the centers of a plurality of said concentric loops are located along a longitudinal axis of said substantially cylindrical member, a plurality of said concentric loops each having a bend with no more than one bend being located in each quadrant of each of said loops, each of said bends in each concentric loop forming an angle, and, along a length of said substantially cylindrical member, a line bisects said angles in a plurality of said bends, said line being substantially parallel to a direction of blood flow through the blood vessel to reduce an impedance of said stent to the blood flow, and wherein the substantially cylindrical member is substantially free of shape memory to permit the substantially cylindrical member to conform to a shape of an interior of the blood vessel.

27. The stent according to claim 26, wherein, when said substantially cylindrical member is implanted in the blood vessel, said line is substantially parallel to a direction of blood flow through the blood vessel.

28. The stent according to claim 26, wherein a number of said angles each has of magnitude and, when said substantially cylindrical member is implanted in the blood vessel, the magnitudes of the number of said angles vary along the length of said substantially cylindrical member to conform to a shape of the blood vessel.

* * * * *